(12) United States Patent
Calvet et al.

(10) Patent No.: US 6,440,997 B2
(45) Date of Patent: *Aug. 27, 2002

(54) –E-2-(3,4-DICHLOROCINNAMYL)-1-CYCLOPROPYLMETHYLPIPERIDINE, AND ITS ANTIDIARRHOEAL USE

(75) Inventors: Alain Calvet, Ann Arbor, MI (US); Maria Chovet, Montrouge (FR); Svein Dahl, Tromsdalen (NO); Henry Jacobelli, Paray-Vieille-Poste; Vassilia Theodorou, Portet-sur-Garonne, both of (FR); Pierre Riviere, San Diego, CA (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,579

(22) PCT Filed: Mar. 4, 1998

(86) PCT No.: PCT/EP98/01564

§ 371 (c)(1), (2), (4) Date: Nov. 10, 1999

(87) PCT Pub. No.: WO98/39296

PCT Pub. Date: Sep. 11, 1998

(30) Foreign Application Priority Data

Mar. 5, 1997 (FR) .............................. 97 02713

(51) Int. Cl.$^7$ ............................. A61K 31/445
(52) U.S. Cl. ........................................ 514/317; 546/192
(58) Field of Search ............................ 514/317; 546/192

(56) References Cited

U.S. PATENT DOCUMENTS 5,849,760 A * 12/1998 Calvet et al. ................ 514/320

OTHER PUBLICATIONS

Burger "Medicinal Chemistry" Wiley–Interscience p. 81 (1971).*

* cited by examiner

*Primary Examiner*—Ceila Chang
(74) *Attorney, Agent, or Firm*—Heidi M. Berven; David R. Kurlandsky; Charles W. Ashbrook

(57) ABSTRACT

(–)E-2-(3,4-dichlorocinnamyl)-1-cyclo-propylmethyl-piperidine of formula I:

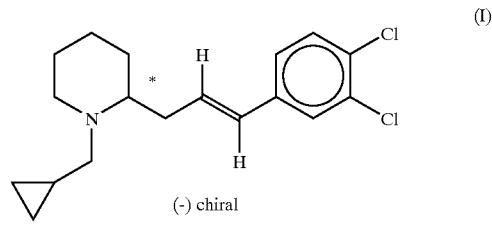

and its pharmaceutically acceptable salts, is useful for treating diarrhea in mammals. Also disclosed are pharmaceutical compositions, processes for preparing compounds of formula (I) and intermediates useful for preparing compounds of formula I.

6 Claims, No Drawings

-E-2-(3,4-DICHLOROCINNAMYL)-1-CYCLOPROPYLMETHYLPIPERIDINE, AND ITS ANTIDIARRHOEAL USE

FIELD OF THE INVENTION

The invention relates to (−)E-2-(3,4-dichlorocinnamyl)-1-cyclopropylmethylpiperidine, its salts, and their use as antidiarrhoeal medicaments in man.

PRIOR ART

The secretory anomalies of the gastro-intestinal tract are responsible, with motor disorders, for the majority of chronic or acute diarrhoeas which, in 1990, were estimated to be the second cause of global mortality, especially in child populations of developing countries.

Chronic diarrhoeas are defined by their generally persistent duration of over two weeks. Their known mechanisms and the diagnostic strategy to be adopted in view of these cases has been documented by M. CERF —Gastroenterol. Clin. Biol, 1992, 16, T 12–T 21. and more recently by M. J. G. FARTHING—Eur. J. of Gastroenterol. & Hepatol. 1996, 8:157–167. The acute diarrhoeas, a great majority of which are of infectious origin, have likewise been documented by M. CERF and M. HAGIAGE: Diarrhées aiguës d'origine infectieuse (Acute diarrhoeas of infectious origin),— Editions Techniques—Encycl. Méd. Chir. (Paris-France), Gastro-entérologie, 9061 $A^{10}$, 1992, 20pp.; and H. L. DuPONT—Review article: infectious diarrhoea—Aliment. Pharmacol. Ther. 1994; 8: pp.3–13. Among other causes, the important role of toxinogenesis during bacterial infection is discussed, and, especially, the expression of the pathogenic capacity by the synthesis of thermolabile or thermostable cytotoxins and enterotoxins, which are responsible for secretory diarrhoeas with a hydroelectrolytic component, and whose representative physiopathological model is that of cholera. Other infectious agents are known to cause diarrhoeas of this type, such as *Salmonella, Escherichia Coli* (*E. coli*) and *Clostridium difficile* (*C. difficile*) strains.

These latter agents, and more particularly *C. difficile*, are responsible for chronic and abundant secretory diarrhoeas, often of nosocomial origin, in subjects submitted to an intensive antibiotic therapy such as HIV positive patients. In the latter, the particularly incapacitating diarrhoeas are often associated with malabsorption, and contribute to the rapid development of an alarming state of denutrition.

For the treatment of secretory diarrhoeas, rehydration of the patients is recommended and sometimes turns out to be essential. Some compounds have been shown to be active (phenothiazine, chlonidine, bismuth salts) but their sensitive employment because of their secondary effects has led to their generalization being abandoned. The usual symptomatic treatments call for adsorbent compounds (Fuller's earth), modulators of the intestinal flora and, very widely, compounds called retardants, which are morphinomimetic antidiarrhoeals: loperamide (INN) and diphenoxylate (INN), known inhibitors of the motility of the GI tract: and, in fact, of controversial if not inadvisable utility for certain ailments, among other reasons through the delay which they contribute to the natural evacuation of pathogenic bacteria.

More recently, it has been proposed to treat these diarrhoeas with acetorphan (INN), a synthetic enkephalinase inhibitor dipeptide with antisecretory effect, which maintains the effect of enkephalins, antisecretory endogenous neuropeptides of the intestinal wall, which are normally rapidly hydrolysed in vivo by the enkephalinases which makes their effect fleeting.

As far as the therapy of diarrhoeas of patients infected with HIV is concerned, it is frequently necessary to resort to serious methods, which can only be carried out in an inpatient environment, such as rehydration and renutrition by the enteral or parenteral routes, which are combined with the symptomatic antidiarrhoeal treatment and an antibiotic therapy directed against the possible pathogenic agent. The usual antidiarrhoeal agents only have, most often, a relative and episodic efficacy. Recently, for these ciiarrhoeas and, more generally, cases resistant to conventional therapy, peptides inhibiting motility and gastrointestinal secretion related to somatostatin have been proposed (M. CAMILLERI—Digestion 1996;57 (suppl 1): 90–92 and M. J. G. FARTHING—Digestion 1996;57 (suppl 1): 107–113). Substitute synthetic compounds for this endogenous mediator are octreotide (INN) and valtreotide (INN), both octapeptides proposed with some success for the treatment of secretory diarrhoeas of AIDS. Although their duration of action is considerably longer than that of somatostatin, these expensive compounds are only active by repeated administration parenterally which leads to prohibitive treatment costs and, because of their mode of administration, makes their use virtually impossible in an outpatient environment. In addition, their lack of specificity, which has been pointed out, can involve secondary effects which dramatically aggravate the state of denutrition of the patients (disorders of the regulation of hydrocarbon metabolism and increase in steatorrhoea).

In addition, certain compounds defined as specific ligands for sigma receptors have shown antisecretory properties suggesting their use in the treatment of diarrhoeas. Thus (+)-N-cyclopropylmethyl-N-methyldiphenyl-1,4-ethyl-1-buten-3-yl-1-amine, or igmesine (INN), and its hydrochloride are disclosed among other compounds in European Patent 0 362 001. The compounds of this patent are defined in vitro as specific ligands for sigma receptors and shown, in vivo, in rats, to be inhibitors of amnesic phenomena caused by scopolamine, and inhibitors of gastroduodenal ulcers caused by the administration of cysteamine, this last activity being connected with their capacity to increase the alkaline duodenal secretion in anaesth,etized animals. In the broad sense, the compounds of this patent are indicated as useful for the treatment of dysfunctions of the gastrointestinal tract such as disorders of peristalsis, of motility, the phenomena of gastro-oesophageal and gastroduodenal reflux as well as for gastric and gastroduodenal ulceration.

Subsequently to these studies, the sigma receptors, whose localization was known in the central nervous system and the immune system, have been demonstrated by F. ROMAN et al. in the gastrointestinal tract of the guinea-pig (Life Sciences 1988, 42, 2217–2222) and then of man (Gastroenterology 1991, 100, A662).

In connection with these localizations, various experiments, among others by J. L. JUNIEN et al. (Neuropharmacology, Volume 30, No. 10, October 1991, pp. 1119–1124) have demonstrated the inhibitory action of igmesine on colonic hypermotility induced by stress via the corticotropin releasing hormone (CRH or CRF) in man. In addition,, P. RIVIERE et al. (Gastroenterol. Clin. Biol. 1991, 15 (2B), A70) show in vitro that igmesine modifies the transmembrane ionic transport through portions of mouse jejunum. This effect, antagonized by haloperidol, involves the participation of sigma receptors. V. J. CARLISI et al. (FASEB J. 1992, 6 (4), A1287) studied the effect of igmesine in vivo in mice, in a model of inflammatory diarrhoea caused by $PGE_2$: at a dose of 30 mg/kg, igmesine, co-administered by the i.p. route with $PGE_2$, delayed by approximately 15 min the appearance of the diarrhoea, an inhibitory effect antagonized by haloperidol, and which, tested for by the oral route, turned out to be zero at a dose of 60 mg/kg. More recently, G. SHI et al. (UEGW 1996—Paris—abstract No. 0786) showed the effect of igmesine at a dose of 200 mg p.o. in man on intestinal hypersecretion induced by $PGE_2$.

On the other hand, the application WO 95/15948 discloses derivatives of 2-arylalkenylazacycloalkanes as ligands for sigma receptors, a process for their preparation and their application in therapeutics. The compounds, their isomers and their addition salts are proposed for the preparation of antipsychotic medicaments and are useful in gastroenterology. The experimental section describes in Example 2E racemic E-2-(3,4-dichlorocinnamyl)-1-cyclopropylmethyl-piperidine and its hydrochloride and, in addition, mentions without specific experimental results that the compounds of the application are active on secretory diarrhoeas induced in mice by Salmonella lipopolysaccharicle (LPS), which suggests their use in the treatment of secretory diarrhoeas of varying aetiologies.

Overcoming the difficulties and uncertainties of the prior art; as set out, the present invention proposes for the purposes of symptomatologic treatment of secretory diarrhoeas the use, in appropriate medicamentous forms, of a novel optically active compound, which is a ligand for sigma receptors, and whose spectrum of antidiarrhoeal properties is particularly remarkable and distinguishes it formally from the prior art.

SUMMARY OF THE INVENTION

The subject of the invention by way of novel compound is optically pure (−)E-2-(3,4-dichlorocinnamyl)-1-cyclopropylmethylpiperidine (I) of formula

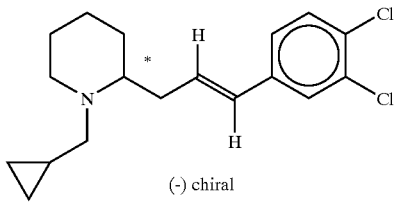

(−) chiral (I)

its addition salts with pharmaceutically acceptable acids and a process for their preparation.

It likewise relates, by way of medicaments, to (−)E2-(3,4-dichlorocinnamyl)-1-cyclopropylmethyl-piperidine (I) and its, addition salts as well as their use in the preparation of pharmaceutical compositions intended for the treatment of diarrhoeas. It also comprises the medicamentous compositions comprising by way of active principle (−)E-2(3,4-dichlorocinnamyl)-1-cyclopropylmethylpiperidine (I) or its addition salts in therapeutically efficacious quantity.

DETAILED DESCRIPTION OF THE INVENTION

In first place, the invention is directed at optically pure (−)E-2-(3,4-dichlorocinnamyl)-1-cyclopropylmethylpiperidine (I) and its addition salts with pharmaceutically acceptable acids.

Optically pure is understood as meaning that the product is practically free of its optical antipode and is at least of an optical purity of 95% and, preferably, equal to or greater than 98% in levorotatory eutomer, this being determined by appropriate analytical means.

Pharmaceutically acceptable addition salts are understood as meaning those inorganic or organic salts, and their possible isomers, shown to be non-toxic in the therapeutically customary doses of which, for example, a list is presented in J. Pharm. Sci., 1977, Volume 66, pp. 119. Non-limiting examples are acetic, benzenesulphonic, camphorsulphonic, citric, ethanesulphonic, hydrdbromic, lactic, maleic, malic, methanesulphonic, mucic, nitric, pamoic, phosphoric, salicylic, stearic, succinic, sulphuric or tartaric acid and hydrochloric acid, which is preferred. In another aspect, the invention relates to a process for the preparation of optically pure (−)E-2-(3,4-dichlorocinnamyl)-1-cyclopropylmethylpiperidine (I) which consists either in resolving the corresponding racemic compound described in Example 2E of the application WO 95/15948, or in carrying out the chemical synthesis starting from (+) E-2-(3,4-dichlorocinnamyl)piperidine (III), itself obtained, according to the application WO 95/15948, by resolution of the corresponding racemic compound described in preparation 2E of the same patent application.

Resolution of the racemic compound corresponding to the product of the invention consists in using an optically active acid to obtain, with the racemate, diastereoisomeric addition salts which are separated by crystallization, and from which the two resolved enantiomers are generated by appropriate treatment. Acids currently used for the preparation of such salts are, as non-limiting examples, the enanticimers of α-phenylglycine, α-phenylalanine, malic, mandelic and tartaric acids, of camphanic acid or alternatively of α-methoxy-α-trifluoromethylacetic acid. An alternative method of resolution is the direct resolution of the racemic compound by high-performance liquid chromatography on a column containing, for example, as stationary phase a cellulose polymer grafted with carbamate groups such as the phase CHIRACEL OD (Daicel) and carrying out an elution with hexane containing a small quantity of triethylamine.

However, the preferred process is an adaptation of the methodology described in the application WO 95/15948 and consists in carrying out the resolution of (+/−) E-2-(3,4-dichlorocinnamyl)piperidine via the eutomeric diastereoisomeric salt with N-acetyl-L-phenylalanine, which, purified and treated, leads to (+) E-2-(3,4-dichlorocinnamyl) piperidine (III), and then in acylating (III) with cyclopropanecarboxylic acid to obtain (+) E-2-(3,4-dichlorocinnamyl)-1-cyclopropanecarbonylpiperidine (II), and then, in reducing (II) with a metallic or organometallic hydride to obtain (−)E-2-(3,4-dichlorocinnamyl)-1-cyclo-propylmethylpiperidine (I) of suitable optical purity and, optionally, in making a pharmaceutically acceptable salt:

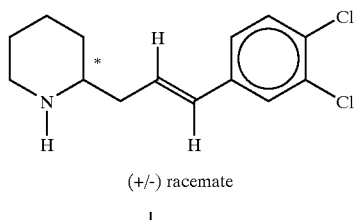

(+/−) racemate

RESOLUTION + N-acetyl-L-phenylalanine

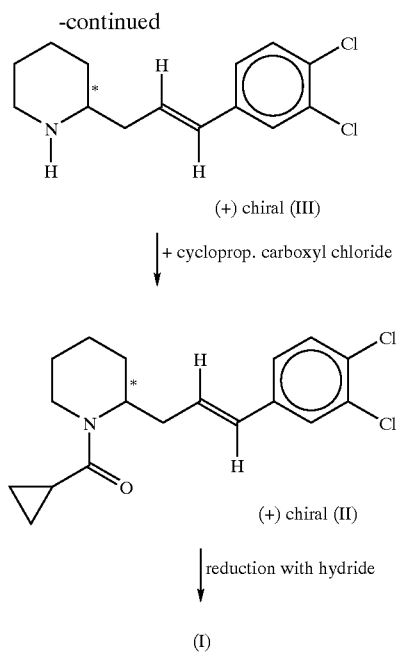

At the resolution stage, the recovery and the purification of the (−) antipode of the intermediate compound (III) allows, according to the same process, the distomer of the compound of the invention to be prepared, namely (+)E-2-(3,4-dichlorocinnamyl)-1-cyclopropylmethylpiperidine synthesized as comparison product.

The compound which is the subject of the invention and its salts have remarkable pharmacological properties, indicative of their usefulness in the form of medicaments for the treatment of secretory diarrhoeas in man. Although in vitro its affinity for sigma receptors is not stereospecific but of comparable intensity to that of its antipode, totally unexpectedly, the (−)E-2-(3,4-dichlorocinnamyl)-1-cyclopropylmethylpiperidine eutomer (I) shows in vivo, in various representative models of toxigenic secretory diarrhoea, a very strong and stereoselective antidiarrhoeal activity.

Thus, the levorotatory eutomer appears from 4 to more than 50 times more active, by the oral route in mice, than its parent racemate in the models of secretory diarrhoea caused by *Salmonella* lipopolysaccharide (LPS), the thermostable toxin of *E. coli* and the A and B toxins of *C. difficile*, without acting on the transit. Likewise, the eutomer turns out to be close to 50 times more active than the racemate by the oral route, in rats, on the inhibition of the intestinal secretion caused by cholera toxin.

In mice, by the oral route in the models of toxigenic secretory diarrhoeas which have just been presented, when it is compared to published compounds or those potentially capable of treating secretory diarrhoeas, the eutomer which is the subject of the invention turns out to be:
  from 66 to more than 4000 times more active than loperamide,
  from 75 to more than 1400 times more active than igmesine,
  and, on diarrhoea caused by LPS, more than 6000 times more active than acetorphan.

Finally, compared to the enantiomers described in the application WO 95/15948 and which turn out to be equally active in vivo in diarrhoea caused by LPS, the study as a function of the dose shows, for the comparison products (−) E-2-cinnamyl-1-cyclopropylmethylpyrrolidine (Example 1.3 of WO 95/15948) and (−) E-2-cinnamyl-1-cyclopropylmethyl-piperidine (Example 2A.3), a progressive effect which, after a maximum, decreases significantly, whereas, differently, the eutomer shows a progressive effect followed by a stage in which this activity is maintained, which is demonstrative of a safety of medical use and of a therapeutic aid, contrary to the comparison products for which the zone of active concentrations, or therapeutic window, is narrow and leads to a dosage which is difficult to handle and thus to a risk of inefficacy.

These studies, expanded on in the experimental section, demonstrate the particularly interesting antidiarrhoeal activity of (−)E-2-(3,4-dichlorocinnamyl)-1-cyclopropylmethylpiperidine (I) and of its salts and their utility in the preparation of pharmaceutical forms which can be administered to mammals including humans by routes appropriate to the pathology and condition of the subject. Thus, the medicaments can be administered by the parenteral, transdermal or transmucosal route in conventionally known forms. However, the pharmaceutical forms adapted to outpatient treatments are preferred and especially those intended for administration by the oral route.

The pharmaceutical compositions according to the invention which contain a therapeutically efficacious quantity of compound (I) or of one of its salts, are appropriate for the treatment of diarrhoeas which may be commonplace, such as those of infants or of travellers, and which may be acute and/or persistent and of varying aetiology in which the secretory component can just as well result from a decrease in absorption as from intestinal hypersecret ion.

Thus, the compositions of the compound (I) are indicated for the treatment of diarrhoeas of inflammatory origin (Crohn's disease, post-radiotherapy enterites), of obstructions by lymphoid hyperplasia or alternatively of anti-cancer chemotherapy.

Likewise, these compositions are appropriate for the symptomatic treatment of hypersecretory diarrhoeas such as those following neuroendocrine tumour conditions (Zollinger-Ellison syndrome, VIPoma, somatostatinoma, carcinoid syndrome), of viral, including HIV, or bacterial infections, or even of congenital dysfunctions or those caused by cathartic drugs, and during hypersecretions of intestinal inflammatory syndromes.

The good tolerance to the product shown in the preliminary tests justifies, for treatments of two to three weeks, a daily dosage of 5 to 50 mg and, in exceptional cases, for aggressive treatments of short duration up to 100 mg. However, the majority of diarrhoeal conditions treated are improved by daily dosages of 10 to 30 mg, the product being administered by the oral route, divided into two to four administrations per 24 hours.

The product is administered in various pharmaceutical forms, containing per unit from 1.25 to 25 mg of the compound (I) or of one of its salts, especially of its hydrochloride; these forms can be, as non-limiting examples, tablets, coated tablets, capsules, gelules, powders, solutions, suspensions or gels.

For the so-called solid forms, the compound (I) or its salt may represent from 1 to 90% by weight of the finished form, the pharmaceutically acceptable excipients representing from 99 to 10%. For liquid forms or those considered as such, the active principle can represent from 0.1 to 10% by weight of the finished form, the liquid phase representing from 99.9 to 90% by weight.

EXPERIMENTAL SECTION

EXAMPLE 1

(−)E-2-(3,4-dichlorocinnamyl)-1-cyclopropylmethylpiperidine (I) and its hydrochloride Stage a): (+) E-2-(3,4-dichlorocinnamyl)piperidine (III)

The compound is prepared by resolution of (+/−) E-2-(3, 4-dichlorocinnamyl)piperidine via the eutomeric diastereoisomeric salt obtained with N-acetyl-L-phenylalanine. In a 500 ml round-bottomed flask equipped with a stirrer and a condenser in the reflux position, 23.00 g (85.1 mmol) of the racemic compound (preparation E2 of WO 95/15948) and 8.82 g (42.6 mmol) of N-acetyl-L-phenylalanine are introduced into 325 ml of acetone.

The mixture is heated to reflux with stirring, and a solution is obtained which is progressively cooled and then kept at 20° C. for 16 hours with stirring. The eutomeric salt is filtered (dry weight: 15.50 g–m.p.=134–141° C.), the filtrate is rendered alkaline and extracted with dichloromethane, and the residual oil from concentration (13.60 g - 50.2 mmol) is salified in the same manner as above in 200 ml of acetone with 6.25 g (30.1 mmol) of Nacetyl-D-phenylalanine. The distomeric salt is removed and the filtrate is treated by rendering alkaline to obtain 7.15 g (26.5 mmol) of residual product which is salified in 150 ml of acetone with 3.57 g (17.2 mmol) of N-acetyl-L-phenylalanine. A second supply of eutomeric salt 6.00 g m.p. 150–152° C. is thus obtained after filtration.

The combined eutomeric salts (21.50 g) are recrystallized for purification in 60 ml of boiling water; 4.30 g of product recrystallize at 20° C. (m.p.=151–152° C.)

The insoluble matter is recrystallized in 60 ml of boiling water; 10.9 g of product (m.p.=153–154° C.) recrystallize at 20° C. The salt is suspended in water, rendered alkaline with a solution of sodium hydroxide and extracted with dichloromethane. The solvent is removed by distillation in vacuo and on a water bath. 6.10 g of product are obtained in the form of a pale yellow oil. Yield=53% $[\alpha]_D^{20}$=+9.600 (c=0.5; dichloromethane)

TLC and NMR in accordance (identical to the racemic starting product)

Stage b): (+)E-2-(3,4-dichlorocinnamyl)-1-cyclopropanecarbonylpiperidine (II)

In a 250 ml reactor equipped with a stirrer and protected from moisture, 6.00 g (22.2 mmol) of (+) E-2-(3,4-dichlorocinnamyl)piperidine (III) obtained in the previous stage are introduced under a nitrogen atmosphere into 100 ml of dichloromethane dried over molecular sieves. 3.40 ml or 2.47 g (24.4 mmol) of triethylamine are added to the pale yellow solution and, after cooling to 10° C., 2.20 ml or 2.55 g (24.4 mmol) of cyclopropanecarbonyl chloride are added in 10 min. The mixture is kept with stirring for 30 minutes at 20–25° C. and then extracted successively with 100 ml of 10% ammonia, 100 ml of 10% hydrochloric acid, 100 ml of saturated sodium bicarbonate solution and finally 100 ml of water. After drying over sodium sulphate, the dichloroimethane is removed by distillation in vacuo and on a water bath. The residual product is obtained in the pure state as a yellow oil. Weight: 7.50 g–yield=100%–$[\alpha]_D^{20}$=+22.600 (c=0.5; dichloromethane)

TLC(CH$_2$Cl$_2$/MeOH 10% ammoniacal 90/10 v/v): Rf=0.90–1.00

Stage c): (−)E-2-(3,4-dichlorocinnamyl)-1-cyclopropylmethylpiperidine (I)

Under a nitrogen atmosphere, protected from moisture and without exceeding 0° C., on the one hand a suspension of 2.65 g (69.5 mmol) of lithium aluminum hydride (LAH) is prepared in 40 ml of dry THF, and on the other hand a solution of 2.99 g (22.4 m mol) of aluminum chloride in 40 ml of dry diethyl ether. After 30 min contact for each preparation, the LAH/THF suspension is introduced in 10 min ago at 0° C. into the ethereal solution of AlCl$_3$, then a solution of 7.40 g (21.9 mmol) of the amide (II) obtained in the previous stage in 30 ml of dry THF is introduced at this temperature and in 10 min. After 30 min at 0° C., the mixture is brought to reflux for 10 min and then cooled rapidly to 0° C. 4.6 ml of 15% (w/v) NaOH solution and then 4.6 ml of water are then added dropwise with caution. After 30 min contact, the mixture is filtered on a buchner provided with a bed of infusorial earth. The filtrate is concentrated in vacuo and on a water bath to obtain (−)E-2-(3,4-dichlorocinnamyl)-1-cyclopropylmethylpiperidine(I) in the form of a yellow oil which is verified pure by TLC. Weight: 3.2 g–yield: 84.6%–$[\alpha]_D^{20}$=67.20 (MeOH, c=8.0)

TLC(CH$_2$Cl$_2$/MeOH 10% ammoniacal 90/10 v/v): Rf=0.65–0.80. 1H-NMR (CDI$_3$- TMS): δ (ppm) 0.00–0.20 (m, 2H) ; 0.40–0.70 (m, 2H); 0.70–1.10 (m, 1H); 1.10–1.80 (m, 6H); 2.10–2.80 (m, 6H); 2.90–3.20 (m, 1H); 6.20–6.40 (m, 2H); 7.10–7.50 (m, 3H).

optical purity>98%, determined by HPLC column 4.6× 150 mm Chiracel ODH 5 μm (Daicel), elution with hexane containing 0.1% of triethylamine, t°=30° C.

Hydrochloride: The base is dissolved in 60 ml of dichloromethane, 7.0 ml of 5.5 N hydrochloric ether are added, and then the solvents are removed by distillation. The solid residue is crystallized by dissolution in an isopropanol/diethyl ether mixture. The white insoluble matter is filtered and dried in vacuo to constant weight. Weight: 5.40 g–yield=68%.

m.p.=182–183° C.–$[\alpha]_D^{20}$=−19.200 (c=0.5; CH$_2$Cl$_2$)

Analysis (C$_{18}$ H$_{24}$ Cl$_3$ N): % C, H, Cl, N in accordance;

IR (KEir): 3400, 2900, 2500, 1450, 1130, 1020, 990, 820, 800 cm$^{-1}$

According to this process, starting from the distomeric salt removed in the resolution in stage a), recovery and purification allow the (−) antipode corresponding to the intermediate compound (III) to be recovered, from which the distomer of the compound of the invention is prepared, namely (+)E 2-(3,4-dichlorocinnamyl)-1-cyclopropylmethylpiperidine, synthesized as comparison product.

EXAMPLE 2

Toxicity Study

In animals, the toxicity study was carried out in mice by the oral route. No mortality was noted up to the strongest dose studied, namely 300 mg/kg. No toxic symptoms were evident at doses lower than 100 mg/kg. Starting from this dose, symptoms were observed such as respiratory depression, trembling, convulsions, a state of prostration or of lethargy which were reversible in a lapse of time of 24 hours after treatment.

EXAMPLE 3

In vitro Pharmacological Study: Affinity for Sigma Receptors

The study of the capacity of interaction with the sigma receptors of the eutomer which is the subject of the invention, of its antipode and of its parent racemic compound, was carried out by the determination of their binding to a rat brain membrane preparation, previously loaded with a labelled ligand specific for sigma receptors, in this; case (+)[3H]-SKF 10,047. The technique used (described by Largent, B. L. et al., J. Pharmacol. Exp. Ther., 1986, vol. 238, pp. 739–748) consists in incubating, in solutions of variable concentrations of the test product, the membrane preparation previously loaded with (+)[3H]-SKF 10,047. After filtration, the radioactivity of the solution, which is representative of the displacement of the ligand by the test: product, is measured. Results are expressed as ICSO of the test product, which is the concentration allowing the tritiated ligand to be displaced from 50% of its binding sites in the membrane preparation Results:: The values obtained are presented in Table 1:

TABLE 1

In vitro study - σ affinity

| Test compound | σ affinity: $IC_{50}$ (nM) |
|---|---|
| (−)E 2-(3,4-dichlorocinnamyl)-1-cyclopropylmethylpiperidine(I) (eutomer) | 17.9 |
| (+)E 2-(3,4-dichlorocinnamyl)-1-cyclopropylmethylpiperidine (antipode) | 21.8 |
| (+/−)E 2-(3,4-dichlorocinnamyl)-1-cyclopropylmethylpiperidine (racemate) | 44.1 |

EXAMPLE 4

In vivo Pharmacological Studies 4-1)—inhibition of experimental toxogenic diarrhoeas Methods a) diarrhoea induced by Salmonella lipoiolysaccharide (LPS):

The test is carried out in mice according to a working procedure, instigated by M. J. CANCIO et al., Gastroenterology November 1992, 103 (5), 1437–43, which in the rat induces, by an endotoxin, alterations in the transport of water and of electrolytes at the colon level.

working procedure: $dBA_2$ male mice (Iffa-credo, les Oncins, France) weighing between 20 and 25 g are placed in individual cages. After adaptation of the animals to their environment, the test product is administered by the oral route in solution or in aqueous suspension and then after one hour (to of the test) an injection of lipopolysaccharides (LPS) of Salmonella enteriditis (Sigma ref. L6761) is carried out in the tail vein at a rate of 15 mg/kg. A preweighed filter paper is then placed under each cage and the weight of faeces eliminated by the animals in two hours ($t_{120}$) is determined. The effect of the test product is determined and is expressed as a percentage of inhibition of the weight of faeces at the dose considered with respect to the weight of faeces of a batch of control animals only having received LPS under the same conditions. These results allow the $ED_{50}$ of the compounds to be calculated, which is the effective dose allowing 50% of the weight of the faeces caused by the administration of the diarrhoeal agent to be inhibited.

b)—diarrhoea induced by the thermostable toxin of E. coli: Nourished male NMRI mice (30–35 g) are weighed and placed in individual cages previously covered with white paper allowing the viewing of the faecal matter voided. The faeces are recovered as soon as voided and are brought together, by periods of 30 min, for 120 min. The faeces thus brought together are weighed before (fresh weight) and after (dry weight) drying at 120° C. for 24 h. The quantity of water present in the faeces is calculated as the difference (fresh weight—dry weight). The thermostable toxin of Escherichia coli (Sigma, E5763) is administered by the oral route at time zero at a dose of 600 U/mouse. The animals of the control batch receive, at time zero, an oral administration of saline. The administration of the test products is carried out by the oral route 1 h before the administration of the toxins. The results are expressed as the quantity of faecal water amassed at time 120 min, and allow the $ED_{50}$ of the compounds to be calculated, which is the effective dose allowing 50% of weight of water of the faeces to be inhibited under the action of the test product.

c)—diarrhoea induced by the A and B toxins of C. difficile: the experimental protocol, the calculation and the expression of the results are identical to those described above. The A and B toxins of C. difficile are administered by the oral route at time zero at a dose of 6 ng/mouse.

Results i)—Compared inhibitory activity of the levorotatory eutomer (I) with the (+/−) parent racemate in mice, p.o administration

TABLE 2

Inhibitory activity

| | $ED_{50}$ (mg/kg) | |
|---|---|---|
| Toxigenic diarrhoea | Laevorotatory eutomer (I) | (+/−) parent racemate |
| Salmonella LPS | 0.0056* | 0.038 |
| E. coil | 0.019 | 0.077 |
| C. difficile | <0.001 | 0.058 |

*inhibitory effect not reversed by naloxone ii)—compared inhibitory activity of the levorotatory eutomer (I) with loperamide (INN), igmesine (INN) and acetorphan (INN) in mice, p.o administration

TABLE 3

Inhibitory activity: $ED_{50}$ (mg/kg)

| Toxigenic diarrhoea | eutomer (I) | loperamide | igmesine | acetorphan |
|---|---|---|---|---|
| Salmonella LPS | 0.0056 | 0.37 | 0.42 | 34 |
| E. coli | 0.019 | 3.92 | 1.72 | N.T. |
| C. difficile | <0.001 | 4.27 | 1.45 | N.T. |

N.T.: not tested iii)—diarrhoea induced by Salmonella LPS: compared inhibitory activity of the levorotatory eutomer (I) with (−)E-2-cinnamyl-1-cyclopropylmethylpyrrolidine (Ex. 1.3 of WO 95/15948) and (−)E-2-cinnamyl-1-cyclopropylmethyl-piperidine (Example 2A.3) in mice, p.o. administration.

TABLE 4

Inhibition of diarrhoea (%)

| | Test product | | |
|---|---|---|---|
| Dose administered (mg/kg) | Levorotatory eutomer (I) | Ex. 1.3 | Ex. 2A.3 |
| 0.00001 | | | ↗ 29 |
| 0.00003 | | | ↗ 45 |
| 0.0001 | | | 65.8 |
| 0.001 | ↗ 7.1 | ↗ 27.9 | ↘ 36.8 |
| 0.003 | ↗ 46.1 | ↗ 63.8 | |
| 0.01 | 59.7 | 78.8 | ↘ 29.5 |
| 0.03 | 59.5 | ↘ 46.7 | |

TABLE 4-continued

| | Inhibition of diarrhoea (%) | | |
|---|---|---|---|
| Dose | Test product | | |
| administered (mg/kg) | Levorotatory eutomer (I) | Ex. 1.3 | Ex. 2A.3 |
| 0.1 | 69.5 | ↘ 12.7 | |
| ED$_{50}$ (mg/kg) | 0.0056 | 0.002 | 0.00004 |

These results demonstrate the therapeutic advantage provided by the compound of the invention, as it shows a significant effect at a dose of 0.003 mg/kg (46.1%), an effect which continues up to a dose of 0.1 mg/kg and beyond. Differently, the comparison compounds only manifest a worthwhile activity within narrow dose limits:

from 0.003 to 0.03 mg/kg (63.8 to 46.7%) for the compound of Example 1.3, from 0.00003 to 0.001 mg/kg (45 to 36.8%) for the compound of Example 2A.3, the activity decreasing considerably at the higher doses for these two compounds.

4-2)—inhibition of intestinal secretion induced by cholera toxin: so-called enteropoolinq technique.

Female Wistar rats (160–180 g) are made to fast from solid food 24 h before the test. At time zero, the animals receive, by the oral route, 0.1 mg/kg of cholera toxin (Sigma, C3012). Three hours afterwards, the animals are sacrificed by cervical dislocation. After median laparotomy, the intestine is ligated at the level of the pylorus and the ileocaecal junction. It is then removed (from the duodenum to the caecum), and weighed full and them empty. The administration of the test products is carried out by the oral route one hour before the administration of the cholera toxin. The results are expressed by weight of intestinal contents and allow the ED$_{50}$ of the compounds to be calculated, which is the effective dose allowing the weight of the intestinal contents to be inhibited by 50% under the action of the test product.

Results

TABLE 5

| Inhibition of intestinal secretion induced by cholera toxin: ED$_{50}$ (mg/kg) | |
|---|---|
| Laboratory eutomer (I) | (+/−) parent racemate |
| 0.038 | 1.9 |

EXAMPLE 5

Pharmaceutical Forms

By way of illustration, the formulation and the preparation of the hydrochloride of the levorotatory eutomer (I) of the invention in the form of capsules and of tablets containing 40 mg of active principle per unit is presented.

5- 1 - Unit formulation of capsules and preparation:

| Hydrochloride of the eutomer (I) | 40.0 mg |
|---|---|
| Lactose | 59.3 mg |
| Colloidal silica | 0.2 mg |
| Magnesium stearate | 0.5 mg |
| Total | 100 mg |

The powders are intimately mixed and then distributed at a rate of 100 mg per unit into capsules of appropriate size.

5 - 2 - Unit formulation of tablets and preparation:

| Hydrochloride of the eutomer (I) | 40.0 mg |
|---|---|
| Lactose | 72.0 mg |
| Hydroxypropylmethylcellulose (HPMC) | 3.6 mg |
| Crosslinked carboxymethylcellulose (CMC) | 3.6 mg |
| Colloidal silica | 0.24 mg |
| Magnesium stearate | 0.6 mg |
| Total | 120 mg |

The active principle is mixed into the lactose and then granulated with the HPMC in solution. The grains are dried and screened on a grid of 1 mm mesh. The CMC and the silica are mixed and then added to the granules. The mixture is then mixed intimately with the magnesium stearate and then compressed at a rate of 120 mg per scored tablet.

What is claimed is:

1. A compound according to formula I which is (−)E-2-(3,4-dichlorocinnamyl)-1-cyclopropylmethylpiperidine and its pharmaceutically acceptable acids.

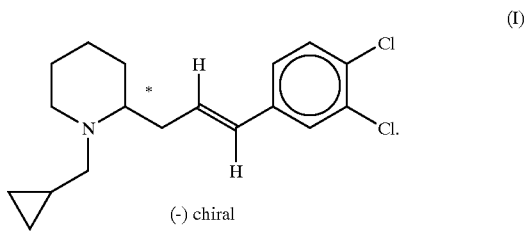

(I)

(−) chiral

2. The hydrochloride salt of claim 1.

3. A process for preparing the compound of claim 1 consisting of:

(a) carrying out the resolution of (+/−) E-2-(3,4-dichlorocinnamyl)piperidine with N-acetyl-L-phenylalanine to provide (+) E-2-(3,4-dichlorocinnamyl)piperidine (III);

(b) acylating compound (III) with cyclopropanecarbonyl chloride to obtain (+) E-2-(3,4-dichlorocinnamyl)-1-cyclopropanecarbonylpiperidine (II);

(c) reducing compound (II) with a metallic or organometallic hydride to obtain (−) E-2-(3,4-dichlorocinnamyl)-1-cyclopropylmethylpiperidine (I); and optionally (d) making the salt of compound (I) with a pharmaceutically acceptable acid.

4. A method of treating diarrhea in mammal, comprising administering to a mammal in need thereof a pharmaceutically acceptable amount of the compound of claim 1.

5. A pharmaceutical composition for treating diarrhea in a mammal, comprising the compound of claim 1 admixed with a pharmaceutically acceptable carrier or excipient.

6. The compounds (+) E-2-(3,4-dichlorocinnamyl) piperidine (II) and (+) E-2-(3,4-dichlorocinnamyl)-1-cyclopropanecarbonylpiperidine (II) for use in preparing the compound of claim 1.

* * * * *